US006576122B1

(12) United States Patent
Bölsing

(10) Patent No.: US 6,576,122 B1
(45) Date of Patent: Jun. 10, 2003

(54) PROCESS FOR THE REDUCTIVE DEHALOGENATION OF LIQUID AND SOLID HALOGENATED HYDROCARBONS

(75) Inventor: Friedrich Bölsing, Lindhorst (DE)

(73) Assignee: DCR International Environmental Services B.V., Amsterdam (NL)

( * ) Notice: Subject to any disclaimer, the term of this patent is extended or adjusted under 35 U.S.C. 154(b) by 0 days.

(21) Appl. No.: 09/496,014

(22) Filed: Feb. 1, 2000

(30) Foreign Application Priority Data

Feb. 2, 1999 (DE) ........................................ 199 03 987

(51) Int. Cl.[7] .......................... C07C 45/00; C07C 17/00
(52) U.S. Cl. .................................. 208/262.1; 208/262.5
(58) Field of Search ........................... 208/262.1, 262.5; 585/464, 641, 642, 733

(56) References Cited

U.S. PATENT DOCUMENTS

| | | | | | |
|---|---|---|---|---|---|
| 4,028,060 | A | * | 6/1977 | Godsey | 436/32 |
| 4,639,309 | A | * | 1/1987 | Lalancette et al. | 208/262 |
| 4,950,833 | A | * | 8/1990 | Hawari et al. | 585/469 |
| 5,197,823 | A | * | 3/1993 | Cutshall et al. | 405/128 |
| 5,345,031 | A | * | 9/1994 | Schwartz et al. | 588/206 |

* cited by examiner

*Primary Examiner*—Thuan D. Dang
(74) *Attorney, Agent, or Firm*—Norris McLaughlin & Marcus

(57) ABSTRACT

1. Process for the reductive dehalogenation of liquid or solid halogenated hydrocarbons.

2.1 Toxic liquid or solid halogenated hydrocarbons such as DDT, HCH, in particular halogenated aromatics such as TCB, PCB, PCP and PCDD/PCDF as such or as contaminants in waste oil or contaminated soil or soil like materials can, in most cases, not at all be dehalogenated or, at best, on a very lavish scale. According to the present invention said halogenated hydrocarbons can be dehalogenated without any problems.

2.2 This can be achieved according to the present invention through transforming the halogenated hydrocarbons as such and the contaminated material respectively into a finely dispersed solid formulation and heating said formulation for a short time with finely dispersed reducing metals.

2.3 Hence, it is for the first time that practice-relevant problems with toxic halogenated hydrocarbons can be solved, in particular with respect to the dehalogenation and thus detoxification of halogenated hydrocarbons in heterogeneous systems, for instance in wet oil, sludge and soil.

21 Claims, No Drawings

PROCESS FOR THE REDUCTIVE DEHALOGENATION OF LIQUID AND SOLID HALOGENATED HYDROCARBONS

The present invention relates to a process for the reductive dehalogenation of liquid and solid halogenated hydrocarbons as such or as contaminants in liquids and solids through chemical reaction with reducing metals in the presence of a hydrogen donating compound characterized in that the halogenated hydrocarbons or the liquids and solids, which contain the halogenated hydrocarbons, are transformed into a finely dispersed pulverulent solid formulation and said finely dispersed pulverulent solid formulation, which contains the halogenated hydrocarbons, is heated up in the presence of a finely dispersed reducing metal and a hydrogen donating compound to a temperature ranging from 80 to 400° C.

Halogenated hydrocarbons in this context are aliphatic, aromatic and mixed aliphatic-aromatic hydrocarbons, which contain at least one halogen in a molecule, including those hydrocarbons, which, in addition to halogen, contain other functional groups, for instance chlorophenols.

Hydrogen donating compounds in this context are all compounds, which can provide hydrogen formally as protons or atomic hydrogen to saturate anions and radicals respectively, for instance alcohols, amines, aliphatic hydrocarbons.

BACKGROUND OF THE INVENTION

Halogenated hydrocarbons are toxic. This can be attributed to the presence of halogen in the molecule. Accordingly, toxic halogenated hydrocarbons can be detoxified through removal of the halogen. Since one single halogen in a molecule can cause a disproportionate high toxicity, it is essential, therefore, to dehalogenate multiply halogenated hydrocarbons in such a way that all the halogen atoms will be removed. This is chemically possible only in case of a reductive dehalogenation.

Halogenated aromatics like polychlorinated biphenyls (PCB), polychlorinated phenols (PCP) and polychlorinated dibenzodioxins and dibenzofurans (PCDD/PCDF) are extremely toxic. PCDD/PCDF, which generally are subsumed under the term “dioxins” are regarded as ultratoxic. Aliphatic halogenated compounds like hexochlorocyclohexane (HCH) or mixed aliphatic-aromatic compounds like trichloro-bis(chlorophenyl)-ethane (DDT) are also toxic even though they are not classified as ultratoxics in general. All these compounds quoted here are, along with other halogenated hydrocarbons, widely spread in the environment. Due to their bioavailability they own a high hazard potential which to abolish must be regarded as an important demand of environmental relevance.

There are a number of processes which deal with the reductive dehalogenation of halogenated hydrocarbons. According to EP 0 099 951 PCB is dehalogenated by means of finely dispersed molten sodium at 100 to 160° C. According to U.S. Pat. No. 4,973,783 halogenated aromatics are reacted with alkali metal in the presence of hydrosiloxane. In U.S. Pat. No. 4,639,309 halogenated hydrocarbons are dehalogenated with sodium or potassium at 100° C. with the aid of mechanical abrasion of the formed halogenides. According to U.S. Pat. No. 4,950,833 halogenated aromatics are reacted with alkali metal in the presence of ammonium salts at 40 to 60° C. and according to the Canadian Application 2026506, in which a whole lot of further processes are quoted referring to the state of the art, halogenated aromatics are treated with finely dispersed sodium or calcium in the presence of methanol, ethanol or isopropanol at temperatures below 100° C. A process of particular effectiveness seems to be described in EP 0 225 849, in which halogenated aliphatic or aromatic compounds are reacted with sodium in an inert solvent in the presence of a $C_1$- to $C_5$-alcohol at temperatures between 100 and 150° C.

The quoted processes have some significant disadvantages. The most important drawback is that said processes are restricted to the use of alkali and alkali earth metals, further in that, as a rule, the reaction temperature must be above the melting point of sodium and that the reaction must be carried out in a homogenous liquid medium in an atmosphere of protecting gas. Said processes are, on no account, applicable to the solution of environmental problems in practice, for instance, to dehalogenate PCB in sludge, dioxins in wet soil, PCP in sand, HCH in a mix of waste material in landfills etc.

Therefore, it would be highly desirable to provide a process efficient to chemically and technically simply dehalogenate halogenated hydrocarbons of whatsoever origin as such or as contaminants in other materials without the restrictions and drawbacks as quoted above.

SUMMARY OF THE INVENTION

In accordance with the present invention there is now provided a process for the reductive dehalogenation of liquid and solid halogenated hydrocarbons as such or as contaminants in liquids and solids through chemical reaction with reducing metals in the presence of a hydrogen donating compound characterized in that the halogenated hydrocarbons or the liquids and solids, which contain the halogenated hydrocarbons are transformed into a finely dispersed pulverulent solid formulation and said finely dispersed pulverulent solid formulation, which contains the halogenated hydrocarbons, is heated up in the presence of a finely dispersed reducing metal and a hydrogen donating compound to a temperature ranging from 80 to 400° C.

DETAILED DESCRIPTION

As reducing metals can be used preferably sodium, magnesium, aluminum and iron but also lithium, potassium, calcium and zinc and the alloys thereof in a finely dispersed form. This finely dispersed form of the metal can be added during the preparation of the finely dispersed, pulverulent solid formulation or during the heating of said solid formulation.

The invention is based on ideas which can be explained most simply by way of an example from practice. For instance, toxic materials such as dioxins, PCB and PCP may be present as contaminants in high concentration in wet soil, which, in addition, is interspersed with oily phases, which also contain toxic halogenated hydrocarbons. In such a case all processes known as chemically applicable to the dehalogenation of halogenated hydrocarbons will fail, because it is not possible to carry out reactions with sodium or potassium in wet soil and because dehalogenating reactions with less reactive metals, like magnesium, aluminum or iron, cannot be used under these conditions. Furthermore, it is impossible to reach the halogenated hydrocarbons in the described heterogeneous mix in order to manage any detoxifying, i.e. dehalogenating chemical reaction. All methods which have been tried so far in order to solve this sort of problem result in an exceptionally costly isolation of the halogenated hydrocarbons, either through extraction with solvents or through thermal stripping processes, for instance in a rotary kiln, and a subsequent high temperature incineration.

However, if the contaminated soil is largely dried thermally or chemically and subsequently disintegrated mechanically to form a pulverulent material, to which a reducing finely dispersed metal along with a hydrogen donating compound and, if necessary, an amine as a reaction accelerator is added and this homogeneous pulverulent mix, which can easily be handled, is heated up for a short time to an appropriate temperature it is possible to dehalogenate the halogenated hydrocarbons because all reaction partners necessary in a dehalogenating reaction are close together in a finely dispersed, i.e. in a highly reactive form. As a matter of fact, the dehalogenation reaction takes place though the reaction is, on closer examination, still a heterogeneous one and it is not easily to recognize, how the halogenated hydrocarbons, adsorptively bonded to the solid particles, can migrate onto the surface of the neighboring metal particles.

However, said course of reaction can be understood if one presumes that the adsorptively bonded halogenated hydrocarbons have access to the metal surface via the gas phase according to their vapor pressure under said reaction conditions. This agrees with the fact that the reaction time can significantly be decreased through the addition of hyperstoichiometric quantities of metal.

The way mentioned in the preceding example to produce a dry pulverulent matrix through a combination of thermal and mechanical processing steps yields good but not optimum results, especially under economic aspects. Best results can be achieved through reacting the oily and wet contaminated soil by means of a dispersing chemical reaction (DCR Technology, e.g. according to DE 23 28 778). For this purpose the contaminated soil is reacted with calcium oxide in a quantity, which is related to the water content present. Said quantity has to be stoichiometric if a complete removal of water is necessary, for instance for a dehalogenating reaction with sodium. The quantity may be significantly lower, for instance about 10 to 15% with respect to the weight of the soil, if metals like iron or aluminum are to be applied for the dehalogenation; in this case the excess moisture in the gas phase does not create any trouble. In a preferential form of implementation the calcium oxide has been rendered hydrophobic.

Calcium oxide can be homogeneously distributed in a wet and oily soil only on the condition that it is strongly hydrophobic. The hydrophobizing compounds should not contain any reducing functional groups in order to avoid a competitive metal consuming. It is of special advantage to render the calcium oxide hydrophobic through the addition of long-chain amines, e.g. stearylamine.

A thermally or chemically pre-dried solid formulation manufactured through grinding or through a dispersing chemical reaction (DCR) can be rendered completely dry through the addition of aluminum alcoholates. Since an alcohol is being formed through the hydrolysis of the alcoholate an additional application of a hydrogen donating compound is not necessary.

On heating a homogeneous pulverulent mix of a solid formulation produced by means of a dispersing chemical reaction (DCR) and a finely dispersed metal a ready and complete dehalogenation will occur.

Amines may be added to the extent of at least 0.1 equivalent per halogen in order to accelerate the dehalogenating reaction with reducing metals. However, this is not necessary if a reaction temperature is applied high enough with respect to the chemical properties of the metal. It seems that under these reaction conditions the thermally induced motions are able to prevent the metal surface from being sealed with reaction retarding layers or to remove such layers.

Amines applicable within the scope of the present invention are aliphatic primary, secondary and tertiary amines or diamines or amines with additional functional groups, in particular amino alcohols, or mixes of said amines or mixes of said amines with hydrogen donating compounds selected from other chemical families.

In case of the application of metals of particular reactivity, e.g. sodium, the residence time necessary in the heating zone will be around some seconds at 200° C. and will increase to the same extent as the temperature decreases. In case an amine is added as an accelerator the residence time will be around 2 seconds at 80° C.

With less reactive metals, such as iron, aluminum, zinc, the residence time is about 2–15 seconds at about 350° C. and will be significantly higher for lower metal concentrations. In these cases the reaction mix will be held in a cyclic process as long as necessary to complete the dehalogenating reaction. An additional application of a hydrogen donating compound with hydrogen in a functional group, e.g. an alcohol, to generate the reduced hydrocarbon from the radical ion intermediate is not necessary, because at said high temperatures hydrogen will be split off even from a mere hydrocarbon compound.

Liquid halogenated hydrocarbons or halogenated hydrocarbons with a low melting point or solutions thereof in liquid inert solvents such as waste oil, transformer oil, hydraulic oil and the like can, in a first step, be dispersed by chemical reaction (DCR), homogenized with metals and further processing aids, i.e. amines and alcohols in a second step, and reacted in a third processing step. It is particularly effective and economic too if less reactive metals, such as aluminum and iron, are suspended in the halogenated hydrocarbons containing liquid, if necessary together with amines and alcohols, and then chemically dispersed by means of calcium oxide (DCR). Thus an extraordinary homogeneous solid formulation is formed in which each collection of agglomerated particles can be regarded as a small reactor in which all reaction partners are extremely intimately packed up together. This pulverulent mix, which can easily be blown, on heating for a short time up to 200 to 400° C., for instance through a momentary contact with a hot metal surface of a reactor, e.g. a solid flow reactor, yields a complete and fast dehalogenation.

Liquid halogenated hydrocarbons or halogenated hydrocarbons with a low melting point or solutions thereof in liquid inert solvents such as waste oil, transformer oil, hydraulic oil and the like cannot be managed in the same way, i.e. in a synchronous dispersing reaction, if reactive metals, such as sodium, are involved. In this case the halogenated hydrocarbons containing liquid must be chemically dispersed separately, if necessary together with amine and alcohol, and the resulting pulverulent dispersion subsequently homogenized with the metal. In this context it is of particular advantage to finely disperse the metal beforehand on any finely dispersed inert carrier, for instance by means of a planetary ball mill, in order to achieve an extremely finely dispersed final mix of both the halogenated hydrocarbons containing dispersion and the finely dispersed reducing metal.

Metals of particular reactivity dispersed on a finely dispersed carrier own pyrophoric properties. For a better handling of such materials they have to be rendered inert through wrapping in inert materials or through mechanical or chemical hydrophobizing.

Halogenated hydrocarbons in sediments, oil sludge and in similar heterogeneous materials can be processed technically more simply if the contaminated material and the reaction partners are worked up separately and mixed finally for reaction. For instance, the heterogeneous halogenated hydrocarbons containing material as well as the mix of amine and alcohol can be transformed, individually, into pulverulent formulations by means of a dispersing chemical reaction (DCR) The resulting finely dispersed pulverulent solid formulations from each dispersing process can be mixed mechanically with the finely dispersed metal. Said final mix is then fed into the reactor for heating. This gives better results than a dispersing reaction directly applied to a mix of all components, i.e. to the heterogeneous contaminated materials along with amine, alcohol and metal.

The finely dispersed metal as such or on a carrier as well as the finely dispersed pulverulent formulations containing the amines and alcohols can be added to the pulverulent solid preparations containing the halogenated hydrocarbons all at once or in portions or continuously during the course of the dehalogenating reaction via a separate reactor inlet.

As regards the technical implementation of dehalogenating reactions the following variants are of practical importance.

Halogenated hydrocarbons present as contaminants in solids, which are free from water or almost free, e.g. ash and filter dust, can be dehalogenated continuously or discontinuously in a reactor tube, in an intensive or compulsory mixer, in a rotary kiln, in a fluidized bed reactor, in a packed solid bed reactor or in a solid flow reactor.

In a matrix free from water sodium can be added; in a matrix which is almost dry magnesium can be added. In an originally water containing matrix sodium can be used only in case the material is thermally or, more advantageous, chemically dried beforehand, for instance through the addition of absorbing agents such as calcium oxide and aluminum alcoholate.

Halogenated hydrocarbons as contaminants in soil or soil-like materials, such as sediments, industrial residues and by-products, which contain water, must be completely dried for a dehalogenation reaction with alkali metals and must be largely dried for a dehalogenation with other metals. For a dehalogenation in a solid flow reactor or in a fluidized bed reactor the matrix must be disintegrated to form a pulverulent material in order to achieve a optimum homogeneous distribution of all reaction partners in the solid matrix.

Drying can be carried out thermally or chemically through the addition of absorbing agents. An appropriate disintegration can be achieved by grinding the dried material. A solid dispersion with optimum properties can be manufactured through disintegration and drying the water containing matrix in one step by means of a dispersing chemical reaction (DCR) using hydrophobized calcium oxide.

The benefits of the present invention can be summarized as follows:

By means of the dehalogenation of halogenated hydrocarbons contained in a finely dispersed pulverulent solid formulation with reducing metals through a short-term heating on temperatures ranging from 80 to 400° C. according to the present invention chemical dehalogenating reactions have been made applicable which otherwise would not allow a complete and economic dehalogenation of halogenated hydrocarbons.

Due to the numerous feasible variants regarding the execution of the dehalogenating reactions according to the invention it is possible now to solve environmental problems with halogenated hydrocarbons in most practice-relevant cases, in particular with halogenated hydrocarbon in waste oil, in oily residues and in polluted soils or soil-like materials even in critical compositions. The reaction temperature necessary to dehalogenate halogenated hydrocarbons within a solid matrix with reducing metals can significantly be decreased through the addition of amines.

EXAMPLES

1. Dehalogenation of PCB in Waste Oil

To 4 g of a waste oil contaminated with 2,9 g (1/100 mol) PCB with 49% Cl 5,4 g diglyme (4/100 mol) was added. This solution was reacted in a DCR reaction with about 4 g of CaO and a substoichiometric quantity of water to form a dry pulverulent product. This finely dispersed dry powder was homogenized with 4 g (2 equ/Cl+100% excess) sodium in the form of a 50% dispersion on an inert solid carrier. In order to completely dehalogenate the resulting homogenous product it was held for about 3 minutes at 120° C., for instance, in a double screw reactor. The hydrogen donating compound can also be added before rendering the finely dispersed dry powder homogenous.

With less reactive metals than Na, K, Li the reaction temperature must be increased. In order to avoid the evaporation of PCB the homogeneous powder must be shock heated, for instance, in a heatable flow reactor.

For a complete dehalogenation with finely dispersed iron, aluminum and zinc the reaction temperatures necessary are 400° C., 370° C. and 220° C. respectively with a residence time of 15 seconds.

2. Dehalogenation of PCB in Waste Oil in the Presence of Amines

To 4 g of a waste oil contaminated with 2,9 g (1/100 mol) PCB with 49% Cl 5,4 g diglyme (4/100 mol) and 0,28 n-butylamine (4/1000 mol) was added. This solution was processed as described in the preceding example. In order to completely dehalogenate the resulting homogenous product it was held for about 3 minutes at 80° C.

With less reactive metals than Na, K, Li the reaction temperature necessary can significantly be decreased through the presence of amines or other hydrogen donating compounds, e.g. triglyme and tetraglyme. In order to avoid the evaporation of PCB even at decreased temperatures the homogeneous powder should be shock heated.

What is claimed is:

1. A process for the reductive dehalogenation of liquid or solid halogenated hydrocarbons in the form of themselves or as contaminants in liquids or solids through chemical reaction with reducing metals in the presence of hydrogen donating compounds which comprises transforming said halogenated hydrocarbons or the liquids or solids contaminated with said halogenated hydrocarbons into a finely dispersed, pulverulent solid formulation and heating said finely dispersed pulverulent solid formulation containing the halogenated hydrocarbons in the presence of a reducing metal selected from the group consisting of lithium, potassium, calcium, sodium, magnesium, aluminum, zinc, iron or an alloy thereof, and a hydrogen donating compound, to a temperature ranging from 80° C. to 400° C.

2. A process according to claim 1, which comprises preparing the finely dispersed, pulverulent solid formulation containing the halogenated hydrocarbons by drying and mechanically disintegrating the halogenated hydrocarbons or the liquids or solids contaminated with them or by subjecting them to a dispersing chemical reaction (DCR).

3. A process according to claim 1 wherein said reducing metal is selected from the group consisting of lithium, potassium, calcium, sodium, magnesium, aluminum, zinc, iron and the alloys thereof.

4. The process according to claim 1, wherein the reducing metal, in the presence of which the finely dispersed, pulverulent solid formulation containing the halogenated hydrocarbons is heated, is in a finely dispersed form on a finely dispersed inert carrier.

5. The process according to claim 4, wherein the formulation comprising the finely dispersed reducing metals lithium, potassium or sodium or the alloys thereof on a finely dispersed inert carrier are rendered inert mechanically or chemically.

6. The process according to claim 1, wherein aliphatic primary, secondary or tertiary amines or diamines or amines with additional functional groups or mixes thereof are added to the finely dispersed mix comprising the solid formulation, containing the halogenated hydrocarbons and the finely dispersed reducing metals.

7. The process according to claim 1, wherein hydrogen donating compounds are added to the mix of the halogenated hydrocarbons containing solid formulation and finely dispersed reducing metals as such or along with amines.

8. The process according to claim 7, wherein the amines and hydrogen donating compounds are added in the form of a finely dispersed pulverulent solid formulation.

9. The process according to claim 7, wherein the finely dispersed pulverulent solid formulation containing the amines and hydrogen donating compounds is prepared by means of a dispersing chemical reaction (DCR).

10. The process according to claim 6, wherein the amines and hydrogen donating compounds and the corresponding finely dispersed solid formulations respectively are added to the reaction mixture comprising the finely dispersed pulverulent formulation containing the halogenated hydrocarbons and the finely dispersed reducing metal all at once or in portions or continuously during the course of the dehalogenating reaction.

11. The process according to clam 1, wherein the finely dispersed pulverulent solid formulation containing the halogenated hydrocarbons is thermally or, through the addition of absorbing agents, chemically completely dried before out the dehalogenation reaction is carried out.

12. The process according to claim 11, wherein calcium oxide or aluminum alcoholate is used as absorbing agent.

13. The process according to claim 1, wherein the dehalogenation reaction is carried out in a heatable reactor tube, in an intensive mixer, in a fluidized bed reactor, in a solid bed reactor or in a solid flow reactor.

14. The process according to claim 6, wherein the reaction mix comprising the finely dispersed solid formulation, the finely dispersed metal and, optionally, the amines and hydrogen donating compounds is prepared in one step by means of a dispersing chemical reaction (DCR) applied to a mix of all starting components.

15. The process of claim 1, wherein said liquids or solids contaminated with said halogenatged hydrocarbons are selected from the group consisting of waste oil, hydraulic oil, transformer oil, condenser oil, filter dust, ashes, soils, industrial byproducts and industrial waste material.

16. The process according to claim 12, wherein the calcium oxide has been contacted with one or more hydrophobizing compounds.

17. The process according to claim 16, wherein the one or more hydrophobizing compounds comprises an alkyl amine having at least 6 carbon atoms, and/or a carboxylic acid having at least 6 carbon atoms, or a salt or an ester of said carboxylic acid.

18. The process according to claim 1, wherein a hydrophobic drying agent or a hydrophobized drying agent is added prior to or during the steps forming the finely dispersed pulverulent material.

19. A process for reductive dehalogenation of liquid or solid samples containing halogenated hydrocarbons, the process comprising the steps of:

contacting a liquid or solid sample containing halogenated hydrocarbons with hydrophobized calcium oxide under conditions permitting formation of a finely dispersed pulverulent material;

contacting said finely dispersed pulverulent material with a finely dispersed reducing metal or alloy thereof, in the presence of a hydrogen donative compound; and holding the resultant mixture at a temperature of 80° C. to 400° C.

20. The process according to claim 19, wherein the hydrogen donative compound is added prior to forming the finely dispersed pulverulent material.

21. The process according to claim 19, wherein the hydrogen donative compound is added concomitantly or after contacting of the reducing metal or alloy thereof, with the finely dispersed pulverulent material.

* * * * *